(12) United States Patent
Ekonen et al.

(10) Patent No.: US 10,676,094 B2
(45) Date of Patent: Jun. 9, 2020

(54) SYSTEMS AND METHODS FOR VEHICLE TO VEHICLE COMMUNICATION AND ALL WHEEL DRIVE DISCONNECT

(71) Applicant: LINAMAR CORPORATION, Guelph (CA)

(72) Inventors: Todd R Ekonen, Brighton, MI (US); Mitchell Holland, Royal Oak, MI (US); William Blake Brown, Canton, MI (US); Matt Griffith, Orion Township, MI (US)

(73) Assignee: Linamar Corporation, Guelph, Ontario (CA)

( * ) Notice: Subject to any disclaimer, the term of this patent is extended or adjusted under 35 U.S.C. 154(b) by 0 days.

(21) Appl. No.: 16/098,920

(22) PCT Filed: May 4, 2017

(86) PCT No.: PCT/US2017/031045
§ 371 (c)(1),
(2) Date: Nov. 5, 2018

(87) PCT Pub. No.: WO2017/192842
PCT Pub. Date: Nov. 9, 2017

(65) Prior Publication Data
US 2019/0176833 A1     Jun. 13, 2019

Related U.S. Application Data

(60) Provisional application No. 62/331,571, filed on May 4, 2016.

(51) Int. Cl.
*B60W 10/02*     (2006.01)
*B60W 30/18*     (2012.01)
(Continued)

(52) U.S. Cl.
CPC ....... *B60W 30/18172* (2013.01); *A61B 17/50* (2013.01); *A61B 17/52* (2013.01);
(Continued)

(58) Field of Classification Search
CPC ....... B60W 30/18172; B60W 50/0097; B60W 10/02; B60W 2720/403; B60W 2710/021; B60W 2550/40; B60W 2550/10
See application file for complete search history.

(56) References Cited

U.S. PATENT DOCUMENTS

2009/0255746 A1* 10/2009 Boesch ................. B60K 6/365
                                                                180/197
2013/0274952 A1   10/2013 Weslati et al.
(Continued)

FOREIGN PATENT DOCUMENTS

DE    102011116112    4/2013
GB         2357159    6/2011

*Primary Examiner* — David J Hlavka
(74) *Attorney, Agent, or Firm* — Miller Canfield (57) ABSTRACT

Methods, devices and systems are provided for determining a connection state of an all wheel drive (AWD) assembly in a vehicle. The method includes receiving, by a vehicle, a message indicative of a hazard and a hazard location on the road and determining a distance to the hazard location from the vehicle. In response to the distance to the hazard location being below a first threshold distance, a state for an AWD assembly in the vehicle is set to a connect state. In response to the distance to the hazard location being above the first threshold, the time for the vehicle to reach the hazard location is determined. If the time to the hazard location is below a threshold AWD connection time, the state for the AWD assembly is set to the connect state.

19 Claims, 8 Drawing Sheets

(51) Int. Cl.
*A61B 17/50* (2006.01)
*A61M 25/00* (2006.01)
*A61F 2/82* (2013.01)
*A61B 17/52* (2006.01)
*A61L 31/02* (2006.01)
*B60W 50/00* (2006.01)

(52) U.S. Cl.
CPC .............. *A61F 2/82* (2013.01); *A61L 31/022* (2013.01); *A61M 25/00* (2013.01); *B60W 10/02* (2013.01); *B60W 50/0097* (2013.01); *A61L 2300/44* (2013.01); *B60W 2554/00* (2020.02); *B60W 2556/45* (2020.02); *B60W 2710/021* (2013.01); *B60W 2720/403* (2013.01)

(56) References Cited

U.S. PATENT DOCUMENTS

2014/0058638 A1* 2/2014 Taniguchi ............. B60W 10/06
 701/69
2018/0141558 A1* 5/2018 Grutter ................. B60K 23/08

* cited by examiner

SYSTEMS AND METHODS FOR VEHICLE TO VEHICLE COMMUNICATION AND ALL WHEEL DRIVE DISCONNECT

RELATED APPLICATION

This application claims priority to U.S. Provisional Application No. 62/331,518, filed on May 4, 2016.

TECHNICAL FIELD

Example embodiments relate to a communications and control system in a vehicle for determining the activation of an all wheel drive system.

BACKGROUND

All wheel drive (AWD) disconnect systems are designed to improve fuel efficiency for an all wheel drive vehicle by disconnecting the major rotating driveline components of an AWD driveline assembly when the performance or benefits of the AWD driveline assembly are not needed. The AWD driveline assembly is preferably connected only if it will likely provide a performance benefit, such as to improve the operation of the vehicle in slippery conditions.

The AWD connect/disconnect system may wait until an undesirable event occurs, such as a wheel slip, and then react by commanding the AWD to connect. Other methods exist for determining or predicting when a connected state of the AWD system will be beneficial based on information received from sensors onboard the vehicle. For example, U.S. Pat. No. 8,095,287 to Beechie describes the use of ambient temperatures and windshield wiper sensor information to determine whether to actuate an AWD system. New communication systems and protocols, such as vehicle to vehicle (V2V) communications and vehicle to infrastructure (V2I) communications, also allow a vehicle to receive information from other vehicles or from structures on or near a road.

SUMMARY

According to one embodiment of the present application there is provided a method for determining a connection state of an all wheel drive (AWD) assembly in a vehicle. The method includes receiving by a vehicle, a message indicative of a hazard and a hazard location; determining a distance to the hazard location from the vehicle; in response to the distance to the hazard location being below a first threshold distance, setting an all wheel drive (AWD) state for an AWD assembly in the vehicle to a connect state; in response to the distance to the hazard location being above the first threshold, determining a time to the hazard location for the vehicle; and in response to the time to the hazard location being below a threshold AWD connection time, setting the AWD state to the connect state.

According to another embodiment there is provided a controller for determining a connection state of all wheel drive assembly in a vehicle. The controller includes a memory; a wireless communications subsystem; and a processor configured to: receive a message indicative of a hazard and a hazard location through the wireless communications subsystem; determine a distance to the hazard location from the vehicle; in response to the distance to the hazard location being below a first threshold distance, set an all wheel drive (AWD) state for an AWD assembly in the vehicle to a connect state; in response to the distance to the hazard location being above the first threshold, determine a time to the hazard location for the vehicle; and in response to the time to the hazard location being below a threshold AWD connection time, set the AWD state to the connect state.

BRIEF DESCRIPTION OF THE DRAWINGS

Advantages of the present invention will be readily appreciated as the same becomes better understood by reference to the following detailed description when considered in connection with the accompanying drawings wherein.

Like reference numerals are used throughout the Figures to denote similar elements and features.

DETAILED DESCRIPTION OF EXAMPLE EMBODIMENTS

The present disclosure is directed to a vehicle and a vehicle controller which is part of an all wheel drive (AWD) connect/disconnect system. An AWD connect/disconnect system is generally designed to improve fuel efficiency by disconnecting major rotating driveline components when the performance or benefits of AWD are not needed. When AWD components are connected, the vehicle typically has better traction and handling characteristics in certain types of conditions. In a connected state, however, fuel efficiency is generally lower due, for example, to parasitic losses. According to the embodiments described herein, the vehicle controller operates to predict when it may be necessary or beneficial to connect components in the AWD driveline assembly based on one or more messages received by the vehicle about the road and its environment. The messages may contain information regarding road conditions, weather conditions, hazards on the road, features of the road, and/or events experienced by other vehicles, any of which may create a situation in which actuating or connecting components in the AWD driveline assembly may be beneficial for the operation of the vehicle. This AWD state is referred to herein as the "connected state". Otherwise, if it is likely not beneficial to connect components in the AWD driveline assembly, it is described herein as a "disconnected" state.

Figure 1:
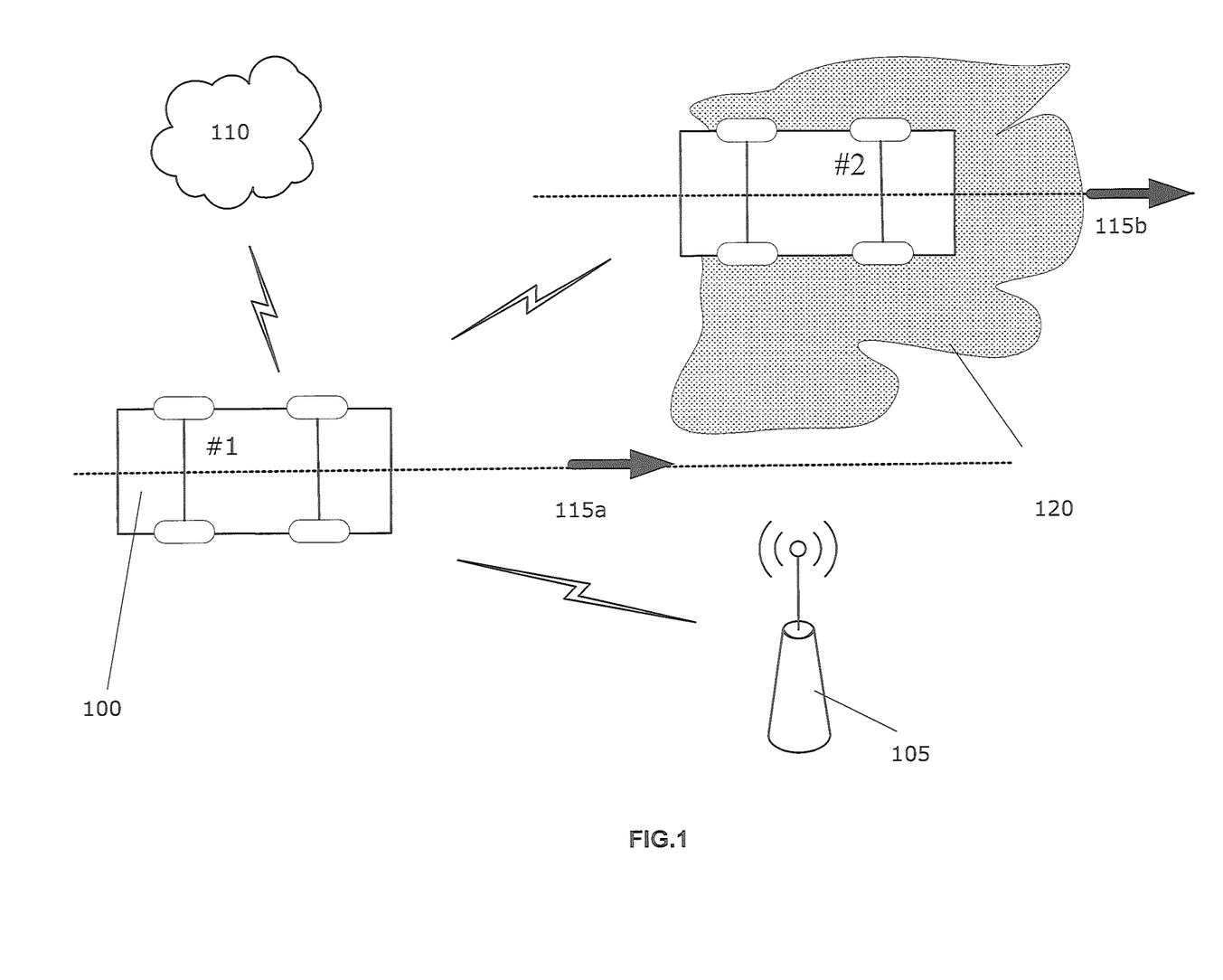
FIG. 1 is a diagram illustrating a vehicle in accordance with one embodiment of the present disclosure and a roadway environment of the vehicle.
Figure 2:
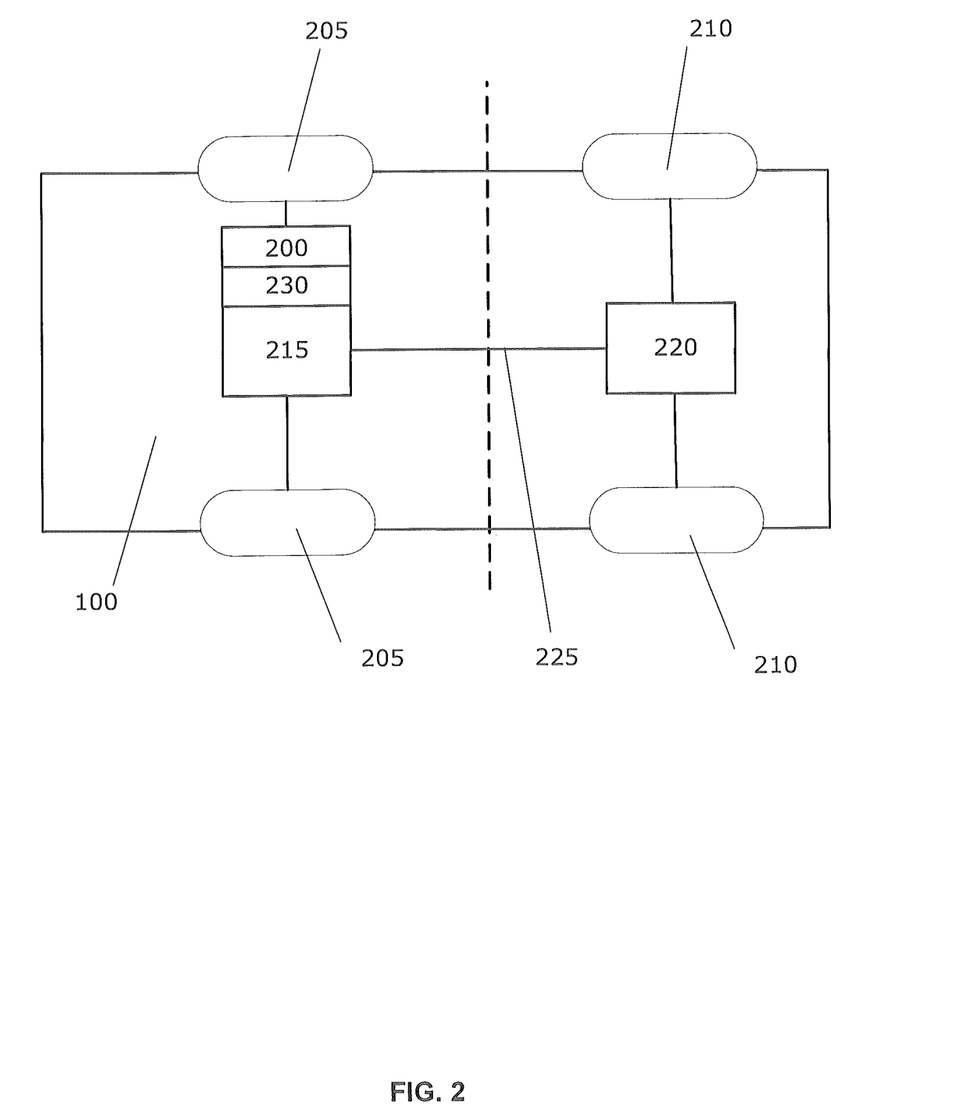
FIG. 2 is a block diagram illustrating a vehicle in accordance with one embodiment of the present disclosure.

An example environment for the operation of a vehicle 100 according to the present application is shown in FIG. 1. The vehicle 100, also labelled as vehicle #1 in FIG. 1, is configured to support one or more types of wireless communications. The messages received by the vehicle 100 may be sent by other vehicles, such as vehicle #2 in FIG. 1.

Vehicle #2 in FIG. 1 may or may not operate according the embodiments described herein but vehicle #2 is at least configured to send wireless communications with the information described herein. The messages received by vehicle 100 may be sent by other structures on or near the roadway, such as a light signal or communication tower, represented by structure 105 in FIG. 1. These types of communications are often referred to as vehicle to vehicle (V2V) communications and vehicle to infrastructure (V2I) communications, respectively, or collectively, V2X communications. Finally, the vehicle 100 may also receive messages about road conditions or features of the road through other wireless communications networks 110, including cellular networks, wireless local area networks such as WiFi™ networks, short range wireless networks such as Bluetooth™ networks, or global positioning system (GPS) networks.

As shown in the example of FIG. 1 by arrows 115a, 115b, vehicles #1 and #2 may be travelling in the same general direction. As vehicle #2 encounters an icy patch 120, it may experience a wheel slip event. As a result, vehicle #2 may transmit or broadcast a message containing information about the slip event and the location of vehicle #2. Upon receipt of the message, and according to methods described herein, vehicle 100 determines whether it is beneficial to set its AWD assembly to a connected state in order to be prepared to handle the same road conditions or "hazard" which caused the slip event for vehicle #2. This determination by the vehicle 100 may be made based on the distance from the vehicle 100 to these road conditions or hazard, and the speed of the vehicle. In some embodiments, the vehicle 100 also may determine the angle between the vehicle's path of travel and the hazard and this angle also may factor into the determination made by the vehicle 100 for its AWD state. In some embodiments, the information received and processed by vehicle 100 may be combined with other information gathered from its internal sensors and components to determine whether the AWD state should be connected or disconnected.

It will be appreciated that the messages transmitted by vehicle #2 may include information regarding one or more features of the road, weather conditions, road conditions, or events, any of which indicate a hazard warranting an AWD connected state. Such information will be referred to herein as an "AWD trigger" since this information may indicate a scenario or "hazard" for which actuation of the AWD assembly may be beneficial. Vehicle #2 may transmit a message containing information about a slip event as described above and the same message or a separate message may contain information indicating an icy road condition exists. Vehicle #2 may determine an icy road condition exists based on information gathered from its sensors and/or information received from other vehicles, structures or networks. In some embodiments, vehicle #2 may retransmit a message it receives from another vehicle (not shown) which includes information of an AWD trigger and a location of the hazard. The vehicle 100 (vehicle #1) may receive multiple messages about one or more potential AWD triggers and hazards including, for example, a message from structure 105 indicating a change in grade, or a particular type of road, such as a gravel road. The message sent by the structure 105 includes either the location of the structure 105 or more particularly, the location of the hazard. The vehicle 100 may receive a message via the wireless communications network 110 about other AWD triggers and hazards such as weather conditions and features of the road.

In some cases, vehicles #1 and #2 do not need to be travelling in the same direction. A message transmitted by vehicle #2 about an AWD trigger and hazard location still may be relevant to vehicle #1 even if vehicle #2 is travelling in the opposite direction from that shown in FIG. 1. Depending on the distances between the vehicles and the hazard, an icy road condition experienced by vehicle #2 still may be relevant to the AWD state for vehicle #1. A change in course for vehicle #1, such as a turn at an intersection, also may bring vehicle #1 into or out of the range of the hazard location for the AWD trigger sent by vehicle #2.

Messages transmitted by vehicles #1, #2, and structure 105 may adhere to the dedicated short range communication (DSRC) standard which is a two-way, short to medium range communications protocol for data transmissions in safety applications. Messages may be received typically within a range of about 1000 feet. DSRC based communications feature very low latency, on the order of milliseconds, fast network acquisition, and high reliability and tolerance to multipath transmissions in roadway environments. DSRC communications are intended to work for vehicles operating at high speeds with an ability to prioritize safety messages and performance abilities that are more immune to extreme weather conditions such as rain, fog, snow etc. DSRC communications may also offer the secure and private transmission or exchange of messages. Messages transmitted and received by vehicles and infrastructure may adhere to the DSRC standard or may be supported by other short range, low latency wireless communications protocols.

Messages transmitted according to the DSRC standard may include a basic safety message (BSM) which contains information about the sending entity such as its location, heading, and speed, as well as a time stamp of the transmitted message. The BSM may be transmitted regularly by each vehicle as a beacon signal.

According to embodiments described herein, vehicles may operate to transmit additional information regarding the status of the vehicle, the road, or events encountered by the vehicle which, as described above, are treated as AWD triggers. In one embodiment, the AWD trigger information may be included as part of the BSM, as part of an extended safety message (ESM), or as part of another message type defined for V2X communications where that message also contains the location of the vehicle and/or the location of the hazard. These messages may be transmitted periodically by each vehicle and/or in response to new AWD trigger information. The AWD trigger information may be encoded in a specific message field, using pre-assigned bit fields or values, or in a predetermined message format.

The AWD trigger information may indicate events experienced by the vehicle transmitting the message such as a wheel slip event, a yaw event (wherein the vehicle's actual yaw rate exceeds a theoretical yaw rate), an anti-lock braking system (ABS) or sudden braking event, a connected or locked AWD state, an accelerator pedal event exceeding a threshold, a change in throttle rate map (such as winter driving mode) due to poor road conditions, a change in state of a torque transfer device due to upcoming road conditions, or a windshield wiper activation. The AWD trigger information may indicate conditions experienced or detected by the vehicle such as a steep grade detected based on throttle position as compared to engine load, a rough road condition as determined by an accelerometer of the vehicle, or a coefficient of friction calculated by the vehicle. The message may indicate AWD triggers such as permanent or semi-permanent conditions or features of the road, including a gravel road, a dirt road, a steep road grade, or a sharp curvature of the road. The message may indicate AWD triggers such as transient conditions or weather conditions including an icy road condition, a snowy road condition, or a rainy or wet road condition. Messages received by the vehicle 100 from the one or more communications networks 110 and/or from infrastructure, such as the structure 105, may include similar AWD trigger information about permanent or semi-permanent conditions or features of the road, map data, and weather conditions, as well as locations for these hazards.

FIGS. 2, 3, 4 and 5 illustrate the vehicle 100, a message-AWD state controller or "MAS" controller 200, and methods executed by the MAS controller 200 based on one or more received messages to determine an AWD state for the AWD driveline assembly of the vehicle 100. As illustrated in the block diagram of FIG. 2, the vehicle 100 has a first set of wheels 205 and a second set of wheels 210. The vehicle includes an all wheel drive (AWD) driveline assembly with a front driveline assembly 215 and a rear driveline assembly 220. The front driveline assembly 215 may include, among other components, an engine, a transmission and a power transfer unit (PTU). The PTU includes an output to transmit torque through a propeller shaft 225 to the rear driveline assembly 220. An all wheel drive (AWD) coupling assembly (not shown) is provided as part of the rear driveline assembly 220 to control coupling and torque distribution between the front and rear driveline assemblies 215, 220. A vehicle supervisory controller 230 is in communication with the MAS controller 200 and with the components in the front and rear driveline assemblies 215, 220. The supervisory controller 230 may also be in communication with one or more sensors (not shown) located throughout the vehicle 100.

Figure 3:
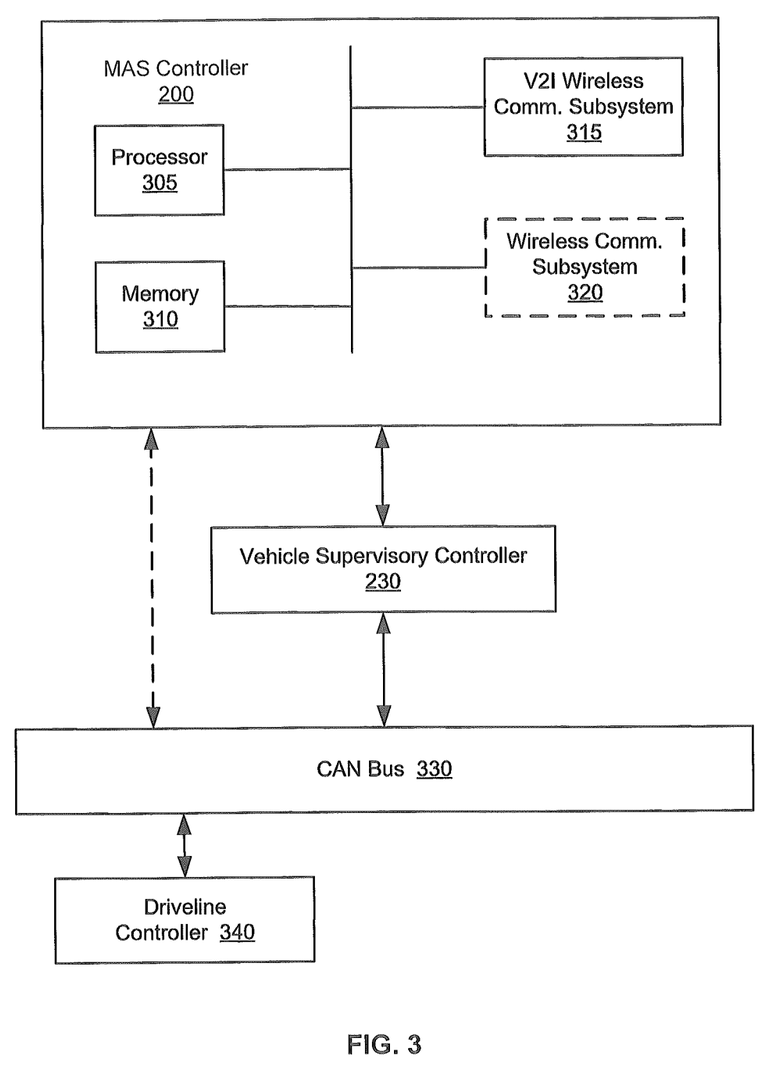
FIG. 3 is a block diagram illustrating a MAS controller and a portion of vehicle control system in accordance with one embodiment of the present disclosure.

FIG. 3 illustrates a block diagram of the MAS controller 200 and a portion of the control system for the vehicle 100. The MAS controller 200 may be a separate component, such as a programmable chip, application specific integrated circuit, or dedicated circuit board assembly or module. The MAS controller may be part of the vehicle supervisory controller 230, or the vehicle supervisory controller 230 may be configured to execute the functions of the MAS controller 200. The MAS controller 200 includes a processor 305 and a memory 310 which is configured to store and execute instructions for methods for determining a connection state of an AWD assembly in the vehicle 100 as described herein. The MAS controller 200 includes at least one wireless communications subsystem, such as a V2X wireless communications subsystem 315 for receiving messages from other vehicles or roadway structures 105. The MAS controller 200 may include additional wireless communications subsystems 320 for receiving messages from the wireless communication networks 110. The V2X subsystem 315 may be configured to receive, or transmit and receive, DSRC communications or other short-range, low latency, safety oriented communication messages as described above. One or more wireless subsystems 320 may be included for supporting cellular communications, wireless local area network communications, such as WiFi™, short range wireless network communications such as Bluetooth™ networks, or GPS communications. The MAS controller 200 may be configured to determine a location or an approximate location of the vehicle 200 based on information received from a GPS network or this action may be performed by the vehicle supervisory controller 230.

The MAS controller 200 may be part of the vehicle supervisory controller 230 or, in some embodiments, the MAS controller 200 may be connected to the vehicle supervisory controller 230. In some embodiments, the connection between the MAS controller 200 and the vehicle supervisory controller 230 may be part of a vehicle communications bus such as a controller area network (CAN) bus 330. The MAS controller 200 also may be connected directly, or via the CAN bus 330, to a driveline controller 340. The driveline controller 340 operates to control the connection state and other aspects of the front and rear driveline assemblies 215, 220 including the actuation of the AWD components.

Figure 4:
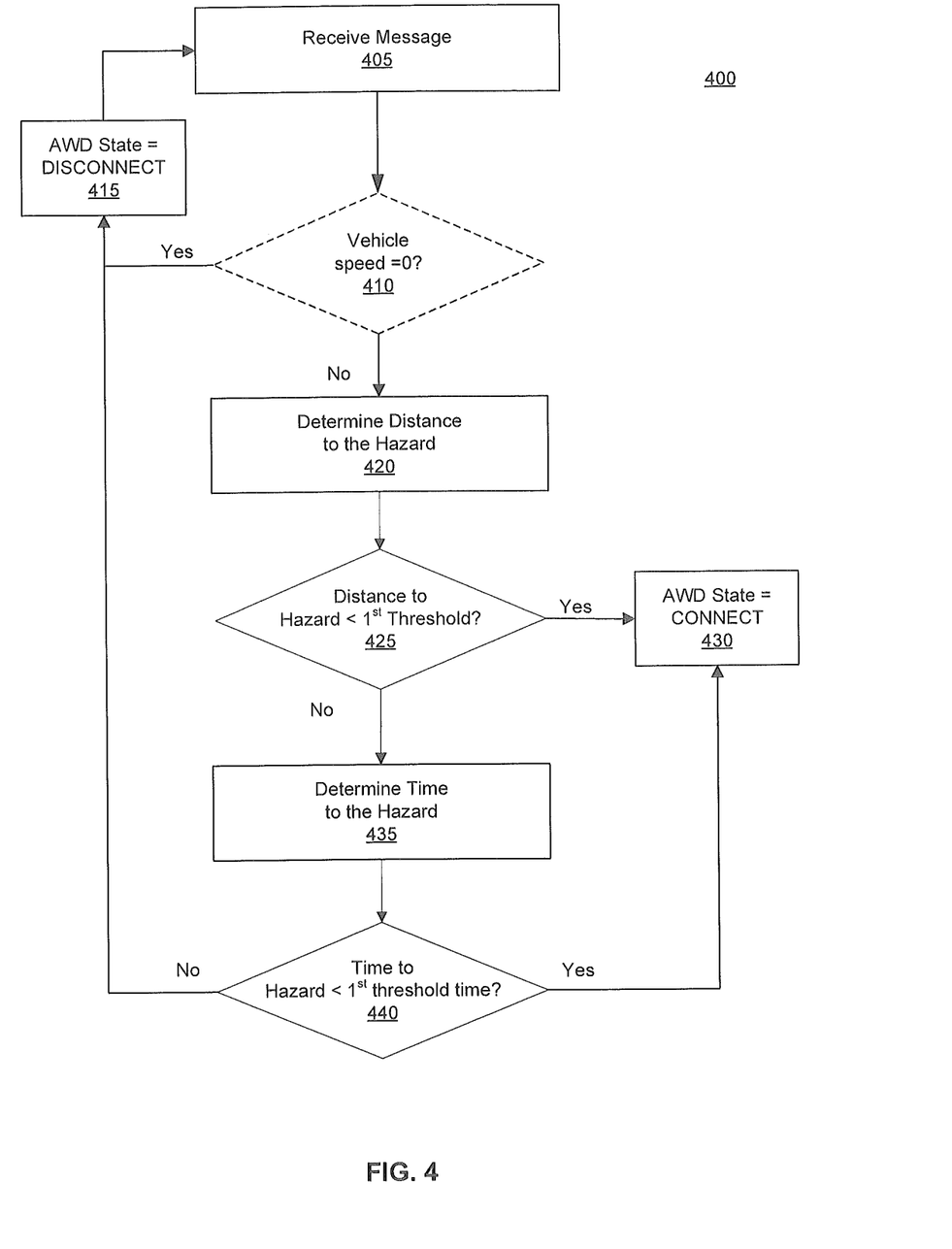
FIGS. 4 and 5 are flow charts of methods for determining a connection state of an all wheel drive (AWD) assembly in the vehicle.
Figure 5:
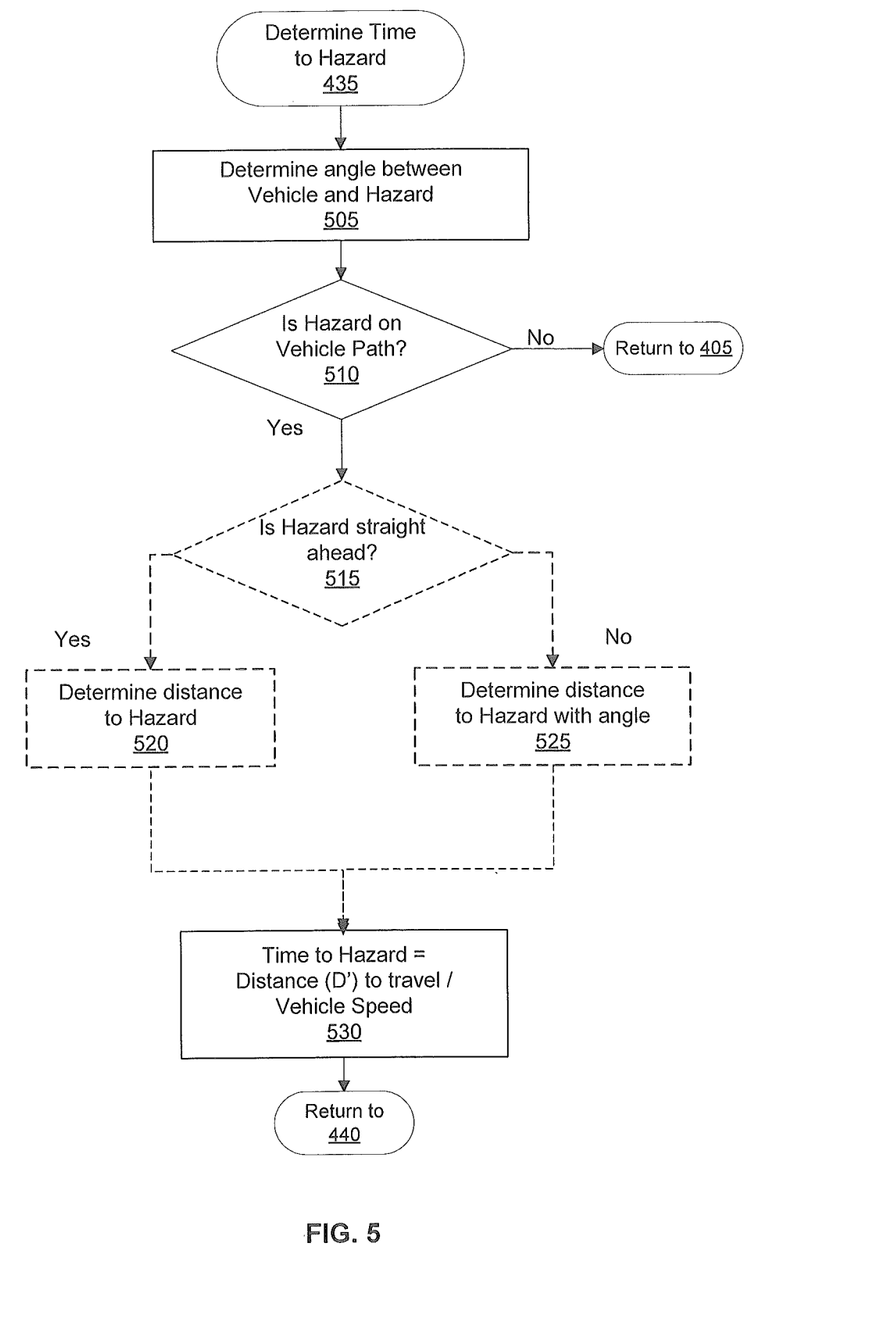

FIGS. 4 and 5 illustrate methods 400, 500 of determining the AWD state for the vehicle 100. The method 400 starts with receiving 405 a message, as described above, which contains AWD trigger information and a location, such as GPS coordinates, of the hazard. The message may be received by the vehicle 100 and immediately processed by the MAS controller 200 or, in some embodiments, the message may be stored in a buffer or queue in memory 310 and retrieved at step 405 for processing. Optionally, if the MAS controller 200 determines 410 that the vehicle 100 is not moving and the vehicle speed is zero, the method 400 may end to eliminate processing time. Alternatively, the MAS controller 200 may set the AWD state to DISCONNECT and return to step 405 to process the next message.

Otherwise, for each message, the MAS controller 200 determines 420 a distance between the vehicle 100 and the location of the hazard as indicated in the message. In one embodiment, the distance (D) between the vehicle 100 and the hazard location is determined by an equirectangular approximation using the GPS coordinates of the vehicle 100 and the GPS coordinates of the hazard. The distance may be determined according to the equation (1) below where $R_E$ is the mean radius of the earth (6,371 km) and X and Y are defined by equations (2) and (3).

$$D = R_E * \sqrt{X^2 + Y^2} \qquad (1)$$

$$X = \Delta\lambda * \cos\left(\frac{\varphi_V + \varphi_H}{2}\right), \text{ and} \qquad (2)$$

$$Y = \Delta\varphi \qquad (3)$$

In the above equations, $\varphi_V$ represents the latitude of the vehicle 100 (in radians); $\lambda_V$ represents the longitude of the vehicle 100 (in radians); $\varphi_H$ represents the latitude of the hazard (in radians); and $\lambda_H$ represents the longitude of the hazard (in radians).

The method 400 includes determining an AWD state based on a comparison 425 of the distance (D) between the vehicle 100 and the hazard, and a first threshold distance. The first threshold distance may be set based on a margin of error in determining locations based on GPS coordinates, as well as the time needed for AWD components to be actuated or connected and operable in the vehicle 100. Thus, for example, if the margin of error for each location is about 4 metres, the first threshold distance may be set to 8 metres. If the distance to the hazard is at or below the first threshold distance, the AWD state is set 430 to CONNECT. The AWD state determined by the MAS controller 200 may be communicated to the driveline controller 340 via the CAN bus 330 in order to actuate and connect the components in the AWD driveline assembly. In other embodiments, the AWD state determined by the MAS controller 200 may be provided to the vehicle supervisory controller 230. The vehicle supervisory controller 230 makes a final determination regarding the AWD state based on the state indicated by the MAS controller 200, as well as other conditions or information received by the vehicle supervisory controller 230 from other components and sensors in the vehicle.

If the distance to the hazard is not within the first threshold distance, the MAS controller 200 determines 435 an approximate time for the vehicle 100 to travel and reach the hazard location. In one embodiment, this time may be determined based on a simple calculation of the distance (D) divided by the vehicle speed. The MAS controller 200 determines the AWD state based on a comparison 440 of the time for the vehicle 100 to reach the hazard, and a first threshold time. The first threshold time may correspond to the time delay associated with the AWD driveline assembly transitioning from a disconnected state to being operable in a connected stated, such as approximately 7 seconds, depending on the vehicle 10. If the time for the vehicle 100 to reach the hazard is below this AWD connection time, the AWD state is set 430 to CONNECT as described above. Otherwise, the AWD state is set 415 to DISCONNECT and the method 400 may end or return to step 405 to process the next message.

Figure 6:
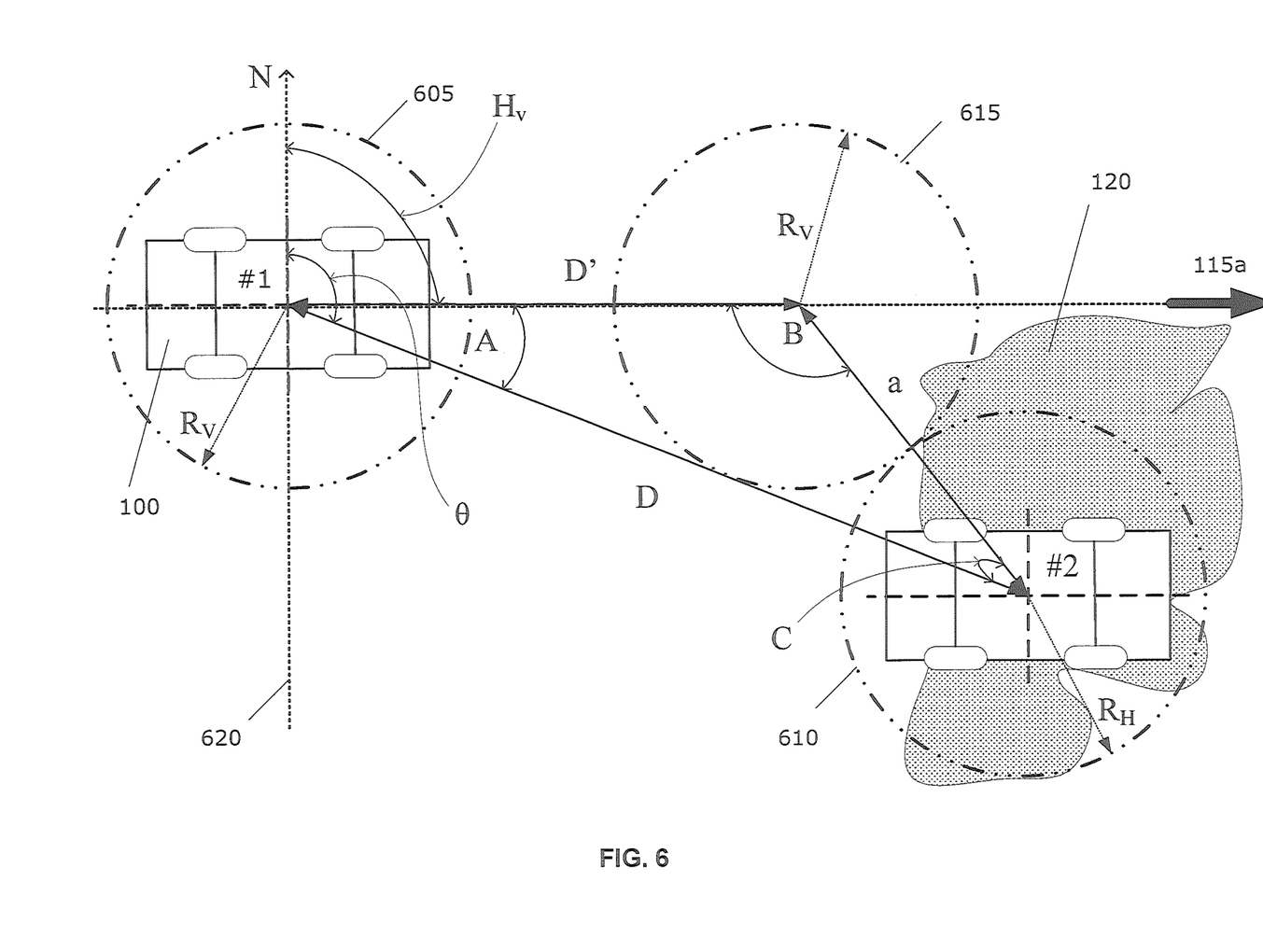
FIG. 6 is a diagram illustrating the vehicle in accordance with one embodiment of the present disclosure and the roadway environment of the vehicle.

FIG. 5 illustrates a further embodiment for a method 435 for determining the time for the vehicle 100 to travel and encounter the hazard location. This determination is made based on an angle between a heading of the vehicle 100 and the hazard location, the distance (D) to the hazard location from the vehicle 100, and the first threshold distance as described above. FIG. 5 will be described with reference to FIG. 6 which illustrates example angles and distances between the vehicle 100 (labelled also as vehicle #1) and a hazard location. FIG. 6 illustrates an example embodiment similar to FIG. 1 in which vehicle #1 is travelling in the direction of arrow 115*a* and has received a message from vehicle #2 about AWD triggers, such as a wheel slip event and/or the icy patch 120 on the road. The current location of vehicle #1 is illustrated by circle 605 which is based on a radius ($R_V$) equal to the margin of error associated with the location of the vehicle 100. In this example, the location of the hazard is deemed to be the same as the location of vehicle #2 which has transmitted one or more messages about the AWD trigger. The location of the hazard is illustrated by circle 610 which is based on a radius ($R_H$) equal to the margin of error associated with the location of vehicle #2. Circle 615 indicates a future position of the vehicle 100 when it is expected to encounter the hazard location within the first threshold distance. The first threshold distance is shown as distance (a) in FIG. 6, where a=$R_V$+$R_H$. As described below, based on an angle (θ) between vehicle #1 and the hazard location, the heading of vehicle #1 as indicated by arrow 115*a*, the distance (D) between the vehicle #1 and the location of the hazard, and the first threshold distance (a), the distance (D') which vehicle #1 will travel before it likely encounters the hazard on its path may be determined.

Returning to FIG. 5, the method 435 includes first determining 505 the angle (θ) between the vehicle 100 and the location of the hazard. In one embodiment, the angle (θ) is determined relative to an axis 620 aligned at true north. The angle (θ) may be determined according to equations (4) through (7) below based on the GPS coordinates of the vehicle 100 ($\varphi_V, \lambda_V$) and the GPS coordinates of the hazard location ($\varphi_H, \lambda_H$), as defined above. In this example, the hazard location is deemed to be the same as the location of vehicle #2.

$$\theta = a\tan 2(X, Y) \text{ where} \tag{4}$$

$$X = \sin(\Delta\lambda) * \cos(\varphi_H), \text{ and} \tag{5}$$

$$Y = \cos(\varphi_V) * \sin(\varphi_H) - \sin(\varphi_V) * \cos(\varphi_H) * \cos(\Delta\lambda) \tag{6}$$

$$\text{and if } \theta < 0, \text{ set } \theta = \theta + 2\pi \tag{7}$$

Based on the angle (θ), the MAS controller 200 determines 510 whether the hazard location is on the path that the vehicle 100 is travelling. Depending on the angle (A) between the hazard location and the vehicle 100, and the vehicle heading, the hazard location may be near the vehicle 100 but it may not be on the path or encountered by the vehicle 100. This determination may be made based on equations (8) through (11) set out below to determine angles A, B and C shown in FIG. 6. As noted above, D is the distance between the vehicle 100 and the hazard location; "a" is the first threshold distance (equaling $R_V+R_H$) at which the vehicle 100 will encounter the hazard location if it continues at its current heading ($H_V$) relative to axis 620.

$$A = |Hv - \theta| \tag{8}$$

$$\text{and if } A < \pi, \text{ set } A = |A - 2\pi| \tag{9}$$

$$B = \pi - \text{asin}\left(D * \frac{\sin A}{a}\right), \text{ and} \tag{10}$$

$$C = \pi - A - B \tag{11}$$

In some embodiments, based on the results of A, B, and C, if B is not real, or if C is less than zero, the MAS controller 200 determines that the hazard location is not on the current path of vehicle #1. The method may end with this determination without setting the AWD state to connect. The MAS controller 200 may continue to step 405 to process the next message. If the hazard location is on the current path of vehicle #1, the MAS controller 200 determines the time for the vehicle #1 to reach the hazard location. In some embodiments, the MAS controller 200 may determine 515 whether the hazard location is directly ahead of the vehicle 100, as indicated by angle (A) equaling zero, or a very small angle. If the hazard location is directly ahead of the vehicle #1, the distance (D') that the vehicle 100 will travel on its path before encountering the hazard location is determined 520 as the distance (D) between the vehicle and the hazard location minus the sum of $R_V$ and $R_H$ (a). If the hazard location is not directly ahead of the vehicle #1, the distance (D') that the vehicle 100 will travel on its path before encountering the hazard location is determined 525 according to equation (12) below.

$$D' = a * \frac{\sin C}{\sin A} \tag{12}$$

Finally, the time for the vehicle 100 to travel before encountering the hazard location is determined 530 based the distance (D') divided by the vehicle speed. The method returns to the action 440 illustrated in FIG. 4 for the MAS controller 200 to determine 440 whether the time to encounter the hazard location is less than the first threshold time.

Figure 7:
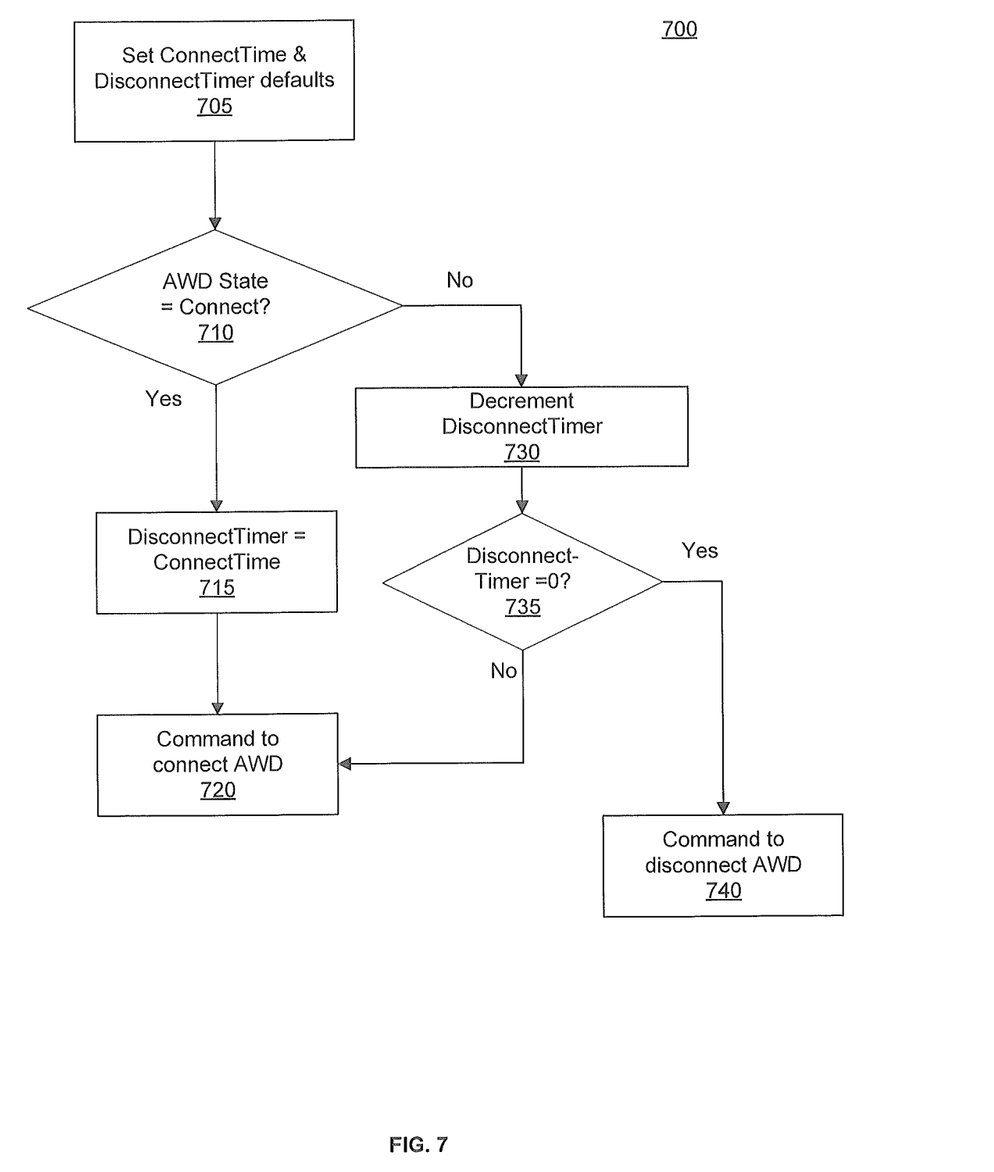
FIG. 7 is a flow chart of a method for determining an AWD disconnect state.

The method 400 may be performed periodically, for example every 100 ms, to process each message received and stored by the MAS controller 200. FIG. 7 illustrates a method 700 for the MAS controller 200 or vehicle supervisory controller 230 to command the connection or disconnection of the AWD driveline assembly based on the AWD state. The method 700 also may be performed periodically, for example every 100 ms. The method 700 includes setting 705 default values for a ConnectTime and a DisconnectTimer. The ConnectTime corresponds to a minimum time that the AWD driveline assembly should remain actuated.

The DisconnectTimer corresponds to the time after which the AWD driveline assembly should be disconnected if no new messages are processed which indicate the connection of the AWD assembly is warranted. These default values for the ConnectTime and DisconnectTimer may or may not correspond to the first threshold time described above.

The AWD state determined by method 400 is checked 710 and if this state indicates a CONNECT state, the DisconnectTimer is reset 715 to the value of the ConnectTime. A command is issued 720 in order to put or maintain the AWD driveline assembly in a connected or actuated state.

If the AWD state is a DISCONNECT state, the DisconnectTimer is decremented by a value dT, which for example, may be set to 0.1 seconds. The DisconnectTimer may be set to a value such as Max(DisconnectTimer-dT,0). If the MAS controller 200 or vehicle supervisory controller 230 determines 735 that the DisconnectTimer has reached zero, a command is issued 740 in order to disconnect components in the AWD driveline assembly. Otherwise, the command is issued 720 in order to put or maintain the AWD driveline assembly in a connected or actuated state. In some embodiments, the vehicle supervisory controller 230 may make a final determination regarding the AWD state based on the DisconnectTimer and method 700, as well as other conditions or information received by the vehicle supervisory controller 230 from other components and sensors in the vehicle.

As described above, the method 400 to determine the AWD state for the vehicle 100 may be performed for each message received by the vehicle 100 from another vehicle or structure or from one or more wireless communications networks 110. In one embodiment, each received message is examined according to the method 800 illustrated in FIG. 8. If the received message provides an indication of a new AWD trigger and hazard location, it may be stored by the MAS controller 200, such as in a buffer in memory 310. The method 400 thus may be run periodically and repeated for each unique hazard location.

Figure 8:
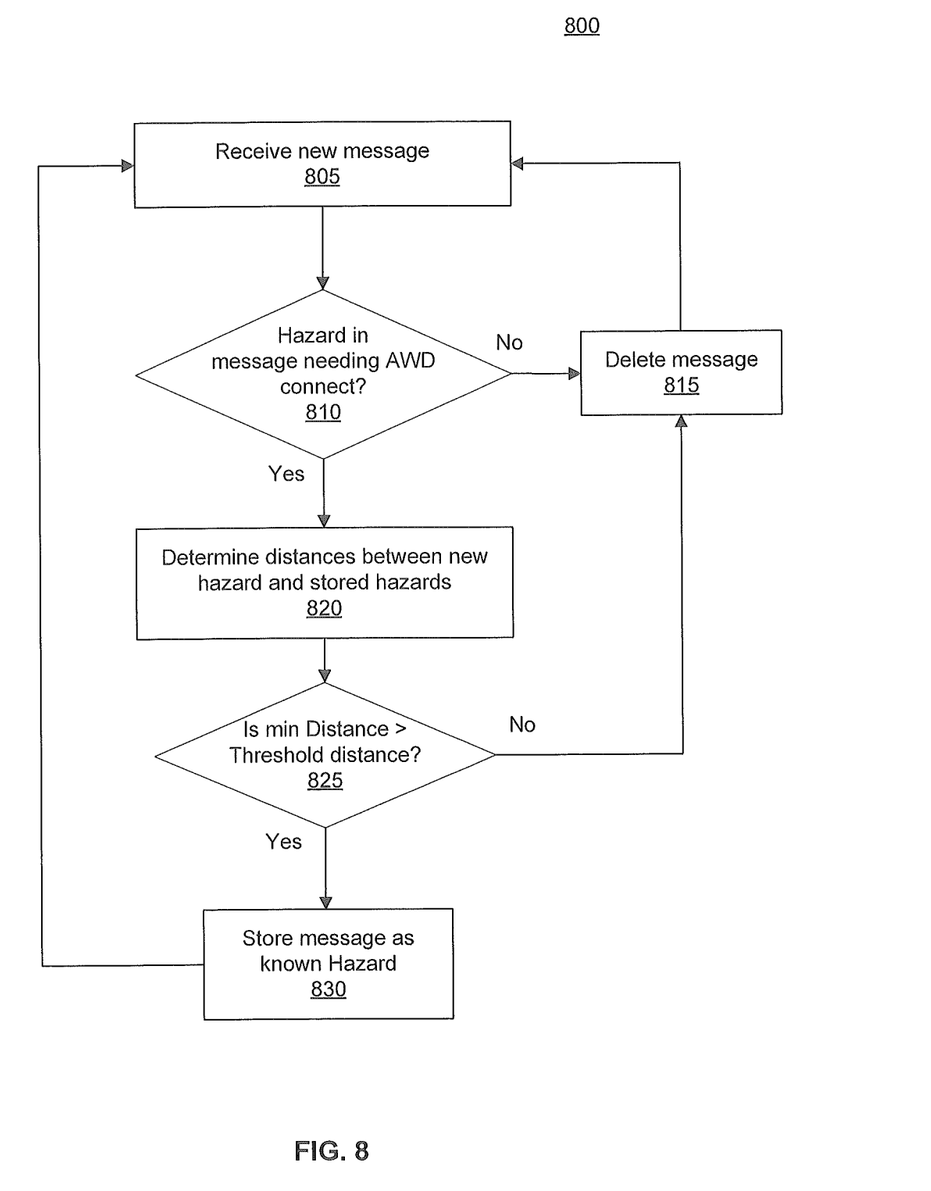
FIG. 8 is a flow chart of a method for receiving messages by a vehicle in accordance with one embodiment of the present disclosure.

The method 800 starts with the vehicle 100 and MAS controller receiving 805 a new message. The new message is examined 810 to determine whether it contains an AWD trigger, i.e. information that may indicate a scenario or hazard for which actuation of the AWD assembly may be beneficial for the operation of the vehicle. In one embodiment, the AWD trigger information may be encoded in pre-assigned bit fields with a value "1" indicating the presence of an AWD trigger and a value "0" indicating no AWD trigger. The bit values may be OR-d together such that if any one or more AWD triggers are present, the method 800 continues. If no AWD trigger is present, the message may be deleted 815. The method continues with the receipt of the next new message.

If the new message includes an AWD trigger, distances are calculated 820 between the location of the new hazard associated with the new message and the locations of hazards stored in the buffer. Distances may be determined based on a GPS location contained in the new message and GPS locations for the existing or known hazards stored in the buffer. The distances may be calculated based on equations similar to equations (1), (2), and (3) described above but using the latitude and longitude of the new hazard location and a stored or known hazard location.

From the calculated distances, a minimum distance is determined. The MAS controller 200 compares 825 the minimum distance with a second threshold distance. If the minimum distance is greater than the threshold, this indicates that the hazard location is not already represented by a previously received message and known hazard stored in the buffer. As a result, the hazard location is stored 830 in the buffer as a known hazard location. The MAS controller 200 may store the complete message, selected fields or data from the message, or just the known hazard location. Otherwise, if the minimum distance is less than the second threshold distance, this indicates that the hazard location is already represented by a previously received message and known hazard location stored in the buffer. In that case, the message is deleted 815. Thus, rather than executing the method 400 to examine every message or every message including the presence of an AWD trigger, the MAS controller 230 may eliminate some received messages in order to reduce the processing time for the method 400. In some embodiments, the second threshold distance also may be set to the same value as the first threshold distance, which may be based on the margin of error in determining locations based on GPS coordinates.

The invention has been described in an illustrative manner, and it is to be understood that the terminology, which has been used, is intended to be in the nature of words of description rather than of limitation. Many modifications and variations of the present invention are possible in light of the above teachings. It is, therefore, to be understood that within the scope of the appended claims, the invention may be practiced other than as specifically described.

The invention claimed is:

1. A method for determining a connection state of an all wheel drive (AWD) assembly in a vehicle, the method comprising:
   receiving by the vehicle, a first message indicative of a hazard and a hazard location;
   determining a distance to the hazard location from the vehicle;
   in response to the distance to the hazard location being below a first threshold distance, setting an all wheel drive (AWD) state for the AWD assembly in the vehicle to a connect state;
   in response to the distance to the hazard location being above the first threshold, determining a time to the hazard location for the vehicle; and
   in response to the time to the hazard location being below a threshold AWD connection time, setting the AWD state to the connect state.

2. The method of claim 1 wherein determining the time to the hazard location comprises:
   determining whether the hazard location is on a path of the vehicle; and
   in response to the hazard location being on the path of the vehicle, determining the time to the hazard location based an vehicle speed and a distance on the path of the vehicle to the hazard location.

3. The method of claim 2 further comprising determining the distance on the path at the vehicle to the hazard location based on an angle between a heading of the vehicle and the hazard location, the distance to the hazard location from the vehicle, and the first threshold distance.

4. The method of claim 1 wherein receiving the first message indicative of the hazard comprises receiving messages from one or more other vehicles, one or more roadway structures, one or more wireless networks, or a combination thereof.

5. The method of claim 1 further comprising,
   receiving one or more second messages;
   determining whether each second message contains information indicative of the hazard and hazard location;

for each second message containing information indicative of the hazard and hazard location, determining a minimum distance between the hazard location based on the second message and the hazard locations stored by the vehicle based on one or more previously received first or second messages; and in response to the minimum distance being greater than a second threshold distance, storing the hazard location of the second message as a new hazard location;

and wherein, determining the distance to the hazard location from the vehicle comprises determining the distance to the new hazard location.

6. The method of claim 1 wherein the hazard location comprises global positioning system (GPS) coordinates of the hazard location, GPS coordinates of another vehicle sending the message indicative of the hazard, or GPS coordinates of a roadway structure sending the message indicative of the hazard.

7. The method of claim 1 wherein the first message comprises an indicator of a wheel slip event in another vehicle, a yaw event in another vehicle, an anti-lock braking system (ABS) event in another vehicle, connected or locked AWD state in another vehicle, an accelerator pedal event in another vehicle, a steep road grade, a rough road condition, a coefficient of friction for the road, a gravel road, a dirt road, a sharp curvature of the road, an icy road condition, a snowy road condition, a wet road condition, or a combination thereof.

8. The method of claim 1 wherein the first message comprises a dedicated short range communication (DSRC) message.

9. The method of claim 1, further comprising activating a connection of the AWD assembly based on the AWD state being set to the connect state.

10. The method of claim 1, further comprising activating the connection of the AWD assembly based on the AWD state being set to the connect state and information received from one or more sensors in the vehicle.

11. A controller for determining a connection state of an all wheel drive assembly in a vehicle, the controller comprising:
a memory;
a wireless communication subsystem; and
a processor configured to:
receive a first message indicative of a hazard and a hazard location through the wireless communication subsystem;
determine a distance to the hazard location from the vehicle;
in response to the distance to the hazard location being below a first threshold distance, set an all wheel drive (AWD) state for the AWD assembly in the vehicle to a connect state;
in response to the distance to the hazard location being above the first threshold, determine a time to the hazard location for the vehicle; and
in response to the time to the hazard location being below a threshold AWD connection time, set the AWD state to the connect state.

12. The controller of claim 11 wherein the processor is further configured to determine the time to the hazard location by:

determining whether the hazard location is on a path of the vehicle; and
in response to the hazard location being on the path of the vehicle, determining the time to the hazard location based on vehicle speed and a distance on the path of the vehicle to the hazard location.

13. The controller of claim 12 wherein the processor is further configured to determine the distance on the path of the vehicle to the hazard location based on an angle between a heading of the vehicle and the hazard location, the distance to the hazard location from the vehicle, and the first threshold distance.

14. The controller of claim 12 wherein the processor is further configured to:
receive one or more second messages through the wireless communications subsystem;
determine whether each second message contains information indicative of the hazard and the hazard location;
for each second message containing information indicative of the hazard and hazard location, determine a minimum distance between the hazard location based on the second message and the hazard locations stored by the controller based on one or more previously received first or second messages; and
in response to the minimum distance being greater than a second threshold distance, store the hazard location of the second message as a new hazard location in the memory;
and, determine the distance to the hazard location from the vehicle by determining the distance to the new hazard location.

15. The controller of claim 12 wherein the hazard location comprises global positioning system (GPS) coordinates of the hazard location, GPS coordinates of another vehicle sending the message indicative of the hazard, or GPS coordinates of a roadway structure sending the message indicative of the hazard.

16. The controller of claim 12 wherein the first message comprises an indicator of a wheel slip event in another vehicle, a yaw event in another vehicle, an anti-lock braking system (ABS) event in another vehicle, a connected or locked AWD state in another vehicle, an accelerator pedal event in another vehicle, a steep road grade, a rough road condition, a coefficient of friction for the road, a gravel road, a dirt road, a sharp curvature of the road, an icy road condition, a snowy road condition, a wet road condition, or a combination thereof.

17. The controller of claim 12 wherein the wireless communications subsystem is configured to receive dedicated short range communication (DSRC) messages.

18. The controller of claim 12 wherein the processor is further configured to activate a connection of the AWD assembly based on the AWD state being set to the connect state.

19. The controller of claim 12 wherein the processor is further configured to activate the connection of the AWD assembly based on the AWD state being set to the connect state and information received by the controller from one or more sensors in the vehicle.

* * * * *

UNITED STATES PATENT AND TRADEMARK OFFICE
CERTIFICATE OF CORRECTION

PATENT NO. : 10,676,094 B2
APPLICATION NO. : 16/098920
DATED : June 9, 2020
INVENTOR(S) : Ekonen et al.

Page 1 of 1

It is certified that error appears in the above-identified patent and that said Letters Patent is hereby corrected as shown below:

On the Title Page

Please change the related U.S. Application data (Item (60)) provisional application number 62/331,571 to provisional application number 62/331,581

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*